United States Patent [19]
Hjertén et al.

[11] Patent Number: 5,814,223
[45] Date of Patent: Sep. 29, 1998

[54] SELECTIVE RECOGNITION OF SOLUTES IN CHROMATOGRAPHIC MEDIA BY ARTIFICIALLY CREATED AFFINITY

[75] Inventors: Stellan Hjertén; Jia-Li Liao, both of Uppsala, Sweden

[73] Assignee: Bio-Rad Laboratories, Inc., Hercules, Calif.

[21] Appl. No.: 961,969

[22] Filed: Oct. 31, 1997

Related U.S. Application Data

[62] Division of Ser. No. 618,879, Mar. 20, 1996, Pat. No. 5,728,296.

[51] Int. Cl.$^6$ .................................................. B01D 15/08
[52] U.S. Cl. ...................... 210/635; 210/656; 210/198.2
[58] Field of Search ..................................... 210/635, 656, 210/198.2, 502.1; 502/402, 404

[56] References Cited

U.S. PATENT DOCUMENTS

| | | | |
|---|---|---|---|
| 5,110,833 | 5/1992 | Mosbach | 521/50 |
| 5,135,650 | 8/1992 | Hjerten | 210/198.2 |
| 5,288,763 | 2/1994 | Li | 521/61 |
| 5,372,719 | 12/1994 | Afeyan | 210/502.1 |
| 5,461,175 | 10/1995 | Fischer et al. | 564/304 |
| 5,541,342 | 7/1996 | Korhonen | 548/532 |
| 5,587,273 | 12/1996 | Yan | 430/269 |
| 5,630,978 | 5/1997 | Domb | 264/330 |

FOREIGN PATENT DOCUMENTS

| | | | |
|---|---|---|---|
| WO 92/13447 | 8/1992 | WIPO | 210/198.2 |
| WO 93/05068 | 3/1993 | WIPO | 210/198.2 |
| WO 95/01347 | 1/1995 | WIPO | 210/198.2 |
| WO 95/21673 | 8/1995 | WIPO | 210/198.2 |

OTHER PUBLICATIONS

Andersson, Enantiomers Resolution on Molecularly Imprinted Polymers Prepared with Only Non–Covalent and Non–Ionic Interactions, J. of Chromatography, 516: 312–322 (1990).

Norrlow O., et al., "Improved chromatography: prearranged distances between boronate groups by the molecular imprinting approach," *Journal of Chromatography*, 396, pp. 374–377, 1987.

Glad, M., et al., "Use of Silane Monomers for Molecular Imprinting and Enzyme Entrapment in Polysiloxane–Coated Porous Silica," *Journal of Chromatography*, 347, pp. 11–23, 1985.

Li, Y., et al., "Continuous Beds for Microchromatography: Cation–Exchange Chromatography," *Analytical Biochemistry*, 223, pp. 153–158, 1994.

Kempe, M., "An Approach Towards Surface Imprinting Using the Enzyme Ribonuclease A," *Journal of Molecular Recognition*, vol. 8, pp. 35–39, 1995.

Hjerten, S., et al., "Molecular Sieve Chromatography of Proteins on Columns of Cross–Linked Polyacrylamide," *Analytical Biochemistry*, 3, pp. 109–118, 1962.

Hjerten, S., "Molecular Sieve Chromatography on Polyacrylamide Gels, Prepared According to a Simplified Method," *Archives of Biochemsitry and Biophysics*, Supplement 1, pp. 147–151, 1962.

M. Kempe, et al., "Separation of Amino Acids, Peptides and Proteins on Molecularly Imprinted Stationary Phases," *Journal of Chromatography A* (Feb. 1995) 691: 317–323.

*Primary Examiner*—Ernest G. Therkorn
*Attorney, Agent, or Firm*—Townsend and Townsend and Crew LLP

[57] ABSTRACT

Chromatographic media that demonstrate an artificially created recognition of any preselected molecular species with only an affinity-type adsorption are formed by polymerization from solutions of non-ionizable monomers with a quantity of the species contained in the solution, followed by removal of the species by conventional washing. The media are of particular utility and interest when used to achieve affinity binding of proteins. Uses of the media include chromatography and the general isolation and removal of the adsorbed species.

12 Claims, 8 Drawing Sheets

SELECTIVE RECOGNITION OF SOLUTES IN CHROMATOGRAPHIC MEDIA BY ARTIFICIALLY CREATED AFFINITY

This is a continuation of application Ser. No. 08/618,879 filed Mar. 20, 1996, now U.S. Pat. No. 5,728,296 the disclosure of which is incorporated by reference.

This invention resides in the field of affinity chromatography, and relates in particular to methods of preparing chromatography supports to impart particular adsorption selectivities.

BACKGROUND OF THE INVENTION

Clinical and laboratory procedures in chemistry and biotechnology frequently rely on the separation of individual species from mixtures of similar species in liquid solutions. Various different types of chromatography, particularly in the high performance mode, are effective and useful methods of accomplishing these separations. Despite the high level to which these techniques have been developed, however, they remain limited to specific types of interactions or by the degree or extent to which species can be separated on the basis of differences in migration rates. There is no known method by which a universal separation medium can be adapted, treated, formed or otherwise tailored to isolate any one selected species from an unlimited variety to the exclusion of all others.

Mosbach and coworkers, as exemplified by U.S. Pat. Nos. 5,110,833 and 5,461,175, have developed what they call "molecular imprinting," which is a method of preparing polymers by polymerizing monomers around "print molecules." Once polymerization is complete, the print molecules are removed, leaving imprints of the print molecules in the polymer. The imprinted polymer then serves as a template to selectively adsorb the same print molecules when subsequently applied, or other molecules or molecular combinations with similar recognition parameters. Mosbach et al. claim that these imprinted polymers can serve the same functions as enzymes, antibodies or chromatographic media.

The monomers are characterized by Mosbach et al. as functional monomers since they bear charged or otherwise functionalized atoms or groups. The resulting polymers are therefore similarly charged or functionalized. The print molecules selected for use are also charged or functionalized in a manner complementary to the functional monomers. The result is a complexation between the polymer and the print molecules. The template retention effect referred to in the preceding paragraph is thus accompanied by, and is in fact secondary to, this smaller scale, molecular-type complexation between the print molecules and individual monomers or their ligand residues.

The work of Mosbach et al. suggests that the molecular imprints left by the print molecules serve only to help retain further such molecules subsequently passed through the gel after these molecules have been drawn into position by the smaller-scale complexation with the ligand or ligands in the imprinting sites. A further suggestion from this work is that to achieve a polymer bearing a molecular imprint one must first form a complex between the print molecule and the monomer. Both suggestions tend to limit the application of "molecular imprinting" as it is currently known to polymers that are not inert, and likewise to print molecules that are not inert, i.e., to monomers and print molecules that form complexes both before polymerization and in the polymer itself.

Another drawback of the use of a functional monomer is that most of the functional monomers, if not all, will be randomly distributed in the polymer gel, and a significant proportion of the functional sites will be at locations other than those where a complex with the print molecule resided during the polymerization to form the gel. Because of these additional functional sites, the gel will exhibit very little specificity, particularly for macromolecules such as proteins which have many adsorption sites that permit attachment of the molecule to the gel in more than one mode. This leads to non-specific adsorption, and the charge on the functional monomers will thus cause the polymer gel to behave as an ion exchanger. For this reason, no polymer gel based on functional monomers has been shown to be highly specific for proteins.

SUMMARY OF THE INVENTION

It has now been discovered that adsorption of molecules to a high degree of selectivity can be achieved in a non-functionalized polymer, i.e., a polymer formed from monomers that do not form complexes with the adsorbed molecules. An affinity chromatography medium in the form of a water-insoluble polymer matrix with selectivity for a preselected molecular species is thus formed from non-ionizable monomers that are chemically and physically inert relative to the molecular species, by polymerizing the monomers in the presence of the molecular species, then extracting the species from the resulting insoluble polymer matrix. The polymer is thus formed without any substantial degree of prior complexation between the molecular species (corresponding to the "print molecule" of Mosbach et al.) and the monomer. Likewise, during use of the polymer thus formed, the adsorption is thus substantially devoid of any electrostatic interaction or other form of complexation between the adsorbed molecular species and individual subunits in the polymer. An advantage of this invention is that adsorbent gels can be prepared that are selective to substantially any molecular species, independent of size, that have a characteristic three-dimensional molecular shape, including species that are ionizable or non-ionizable, those bearing functional groups and those lacking functional groups.

Further features and advantages of this invention will become apparent from the description that follows.

BRIEF DESCRIPTION OF THE DRAWINGS

FIG. 6a is a chromatogram of a test sample, FIG. 6b is a chromatogram of the fraction collected upon passing the sample through a blank column, and FIG. 6c is a chromatogram of the fraction collected upon passing the sample through a column prepared according to Mosbach et al.

DETAILED DESCRIPTION OF THE INVENTION AND PREFERRED EMBODIMENTS

Figure 1A:
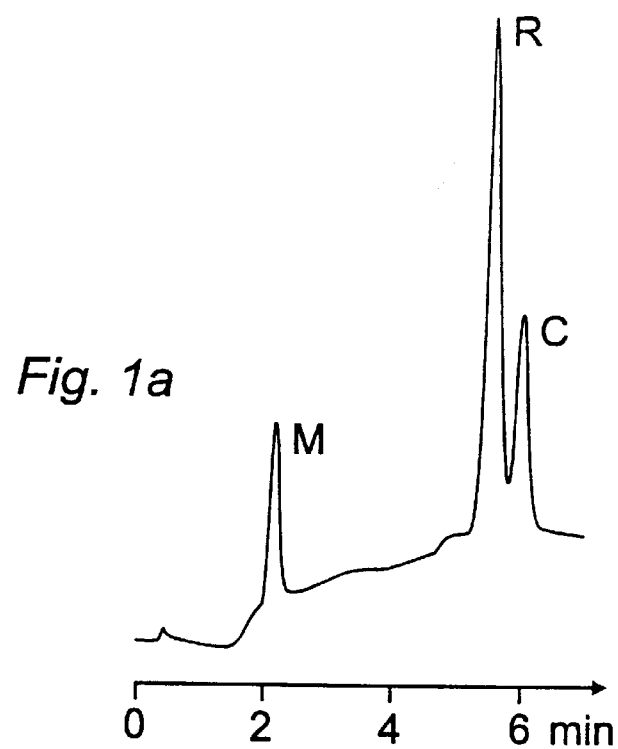
FIG. 1a is a chromatogram of test sample containing a mixture of proteins prior to passage through a gel affinity column.

Gels for use in the present invention may be formed from any conventional material, particularly those known to be useful in forming an electrophoresis or chromatography gel, or chemical analogs of such materials, provided that the materials do not contain charged groups, either in their native form or by virtue of ionization. Thus, gels containing amine groups or carboxylic acid groups are excluded, while gels containing esterified acid groups, amide groups, hydroxyl groups and other non-ionizable groups fall within the scope of this invention. Examples of gel-forming materials are acrylamide, agarose, methacrylate, starch, and any of various substituted acrylamides, acrylates and methacrylates, provided that the substituents are non-ionizable. Examples of substituents are hydroxyl groups and alkyl groups. A specific example of a substituted acrylamide is N-methylol acrylamide. Specific examples of substituted methacrylates are methyl methacrylate and 2-hydroxyethyl methacrylate. The gel-forming material may be a monomer such as acrylamide, methacrylate or a substituted methacrylate, or a non-crosslinked polymer such as agarose that can be crosslinked to form a gel. Combinations of these gel-forming materials can also be used. Examples are agarose combined with acrylamide or a substituted acrylamide, agarose combined with methacrylate or a substituted methacrylate, and acrylamide-methacrylate combinations.

Aside from the inclusion of the non-reacting species to which the gel will demonstrate specific adsorptivity, the gel mixture is formulated and reacted in the conventional manner. Crosslinking agents and polymerization or crosslinking catalysts can be included as needed to achieve a gel of the desired density, porosity and consistency. polyacrylamide gels, for example, can be crosslinked with N,N'-methylenebisacrylamide, piperazinediacrylamide, ethylene diacrylate, diallyltartardiamide, or N,N'-bisacrylylcystamine. Agarose gels can be crosslinked with divinyl sulfone or bis-epoxides. Examples of initiators (catalysts) to form polyacrylamide gels are N,N,N',N'-tetramethylethylenediamine and ammonium persulfate (in combination), riboflavin, and β-dimethylaminopropionitrile.

The gel concentration, i.e., the concentration of monomers or prepolymers, including crosslinking agents if present, in the gel-forming solution, can vary widely, provided that the resulting gel has sufficiently structural integrity for the particular form of chromatographic medium in which the gel will be used. The gel can be porous or macroporous if it fills the entire separation column, or it can be formed outside the column and granulated prior to insertion into the column, in which case the gel can be porous, macroporous or nonporous. The gel concentration, particularly with acrylamide gels, is conveniently expressed as the weight of monomer or prepolymer and crosslinker in grams, divided by the volume of solution in milliliters, multiplied by 100. The result is represented by the symbol "T," in percent (weight/volume). In preferred embodiments of this invention, T ranges from about 1% to about 60%. More preferred are those in which T is in the range of about 2% to about 30%, and most preferred are those in which T is in the range of about 3% to about 10%. When a crosslinker is present, the crosslinker concentration is conveniently expressed as the weight of crosslinker divided by the combined weight of monomer or prepolymer and crosslinker, multiplied by 100. The result is represented by the symbol "C," in percent (weight/weight). In preferred embodiments of this invention, C ranges from about 0.2% to about 60%. In embodiments of this invention with low crosslinker amounts, a particularly preferred range of C is about 1% to about 10%. In embodiments with high crosslinker amounts, a particularly preferred range of C is about 30% to about 55%.

Species that give the gel its characteristic recognition capability in accordance with this invention can be any substance having a distinctive three-dimensional shape and that will not react or form a complex, or will react or form a complex at most only slightly, with any component in the gel-forming solution under the conditions required for gel formation. The species can be either ionizable or non-ionizable. Species to which this invention is applicable range from small molecules having a molecular weight of less than 100 daltons to bodies such as viruses and bacteria. presently preferred species are single-molecule species having molecular weights of at least about 100, and preferably from about 100 to about 1,000,000. Organic compounds, including nucleic acids and carbohydrates, are of particular interest, and biological molecules, particularly proteins, are of greatest interest. preferred proteins are those having molecular weights within the range of about 3,000 to about 300,000, and particularly preferred are those having molecular weights within the range of about 10,000 to about 100,000. Examples of the types of proteins that can be used are enzymes, immunoglobulins and other globulins, storage proteins, transport proteins, contractile proteins, hormones, globular and fibrous proteins, and simple and conjugated proteins.

The quantity of the selectivity-defining species present in the gel-forming solution during the gel formation is not critical and can vary considerably. The choice between a high or low concentration may however affect the adsorptive capacity of the resulting gel. In a typical application, the weight ratio of the selectivity-defining species to the gel-forming materials (i.e., the monomer or prepolymer, plus crosslinker if present) will range from about 0.003:1 to about 5:1, preferably from about 0.03:1 to about 0.5:1.

Following formation of the gel, the selectivity-defining species is removed in a manner that leaves the chemical composition and structure and the three-dimensional conformation of the gel intact. In many cases, this can be achieved by simple washing of the gel with a buffer solution. In cases where the adsorptive affinity between the gel and the adsorbed species is particularly strong, a buffer with a high ionic strength will serve more effectively as a wash solution. For species that are strongly adsorbed proteins, a denaturing agent may be included. Examples are sodium dodecyl sulfate, N-lauryl sarkosine, deoxycholate, and urea. The same desorbing agent can be used subsequent to the adsorption of the species from a liquid sample, to remove the adsorbed species for quantification purposes or to regenerate the gel for repeated use.

Desorption can also be achieved by enzymes degrading the species. This is useful for those molecules that are more strongly adsorbed. One type of gel in which this might be useful is a gel in which one of the gel-forming components reacts to a limited extent with the selectivity-defining species. For example, divinyl sulfone when used as a crosslinking agent will react with the amino groups in a hemoglobin molecule when the latter is used as the selectivity-defining species. The reaction will result in some hemoglobin molecules becoming covalently attached to the gel bed and thus incapable of being removed by simple washing. The effect is only a minor one, since most of the hemoglobin will not react in this manner and the gel will be left with an adequate number of recognition sites. Nevertheless, the small amount of covalently attached hemoglobin can be removed by enzymatic action.

The applicability of this invention varies widely. The gels thus prepared can be used for the simple isolation of one or several species from a biological mixture or from chemical mixtures in general for identification or quantification purposes, or for obtaining a purified or concentrated solution of the species. The gels can also be used to remove one or more specified species from a liquid solution. Other uses, including biosensors, will be readily apparent to those skilled in the art. Note that this invention is not limited to use of a single molecular species as the print molecule. Gels within the scope of this invention can be formed around two or more distinct molecular species, the resulting gel exhibiting selectivity toward all of these species.

The following examples are offered for purposes of illustration, and are intended neither to define nor to limit the invention in any manner.

EXAMPLE 1

This example illustrates the preparation of a polyacrylamide gel with specific affinity for cytochrome C and its effectiveness in selectively adsorbing cytochrome C relative to two other proteins, myoglobin and ribonuclease.

Cytochrome C (10 mg) was dissolved in 1 mL of deionized water, and acrylamide (57 mg), N,N'-methylenebisacrylamide (3 mg) and 10 $\mu$L of a 10% (weight/volume, i.e., 10 mg of solute per 100 $\mu$L of solution) aqueous ammonium persulfate solution were added. The solution thus had a total monomer concentration (T) of 6% and a crosslinking concentration (C) of 5%. The solution was deaerated for 1 minute, and 10 $\mu$L of 5% N,N,N',N'-tetramethylethylenediamine (TEMED) were added. polymerization was allowed to proceed overnight.

The resulting gel was pressed through a 100-mesh net and packed into a pasteur pipette (internal diameter 5 mm; length of gel in column 4.0 cm) fitted with a glass wool support at the constriction. The gel-filled column was then washed overnight with a 10% (volume/volume) solution of acetic acid containing 10% (weight/volume) sodium dodecyl sulfate. The column was then equilibrated with 10 mL of 0.01M sodium phosphate (pH 6.2) to prepare for the elution.

A second column was prepared in a manner identical to the first, but without cytochrome C.

A starting protein mixture consisting of equine myoglobin (1.0 mg/mL), ribonuclease A (4 mg/mL) and cytochrome C (1.0 mg/mL) was used as a test mixture. Following equilibration of both columns, about 50 $\mu$L of the test mixture was applied to each column. Non-adsorbed proteins were then eluted with the same buffer used to equilibrate the columns. The non-adsorbed proteins eluted from the columns were collected in 1-mL fractions.

The non-adsorbed proteins were analyzed by high-performance cation-exchange chromatography, using a Bio-Rad CB-S HpLC column (7.9 mm internal diameter×20.3 mm length, available from Bio-Rad Laboratories, Hercules, Calif., USA), which had been equilibrated with 0.01 sodium phosphate (pH 6.2). For each analysis, about 75 $\mu$L of the 1-mL fraction of non-adsorbed proteins was applied to the column. The same analysis was also performed on the test mixture itself prior to application to either column. The chromatograms were developed with a 5-mL linear sodium chloride gradient from 0 to 0.5M sodium chloride. Detection was performed at 220 nm.

Figure 1B:
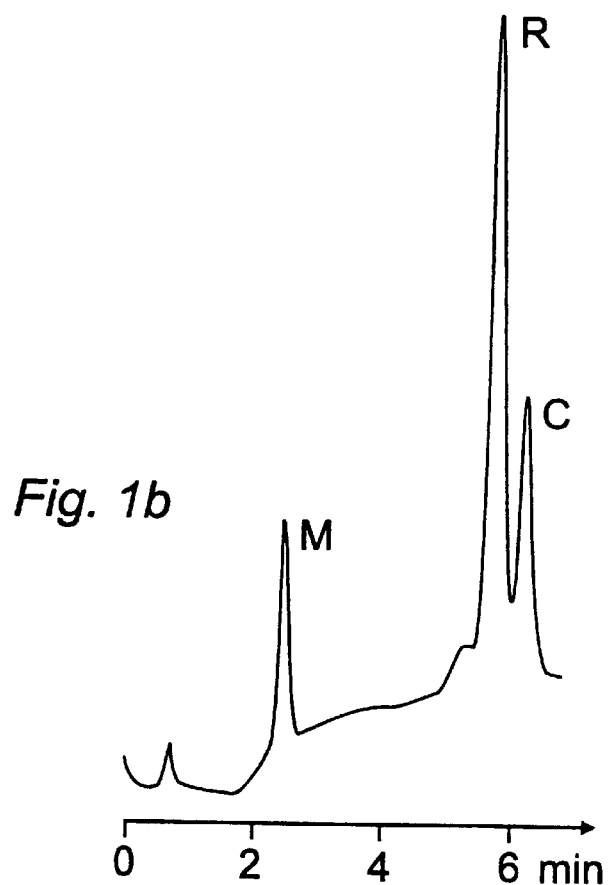
FIG. 1b is a chromatogram of the non-adsorbed protein fraction of the same test sample, the fraction having been obtained by passing the sample through a gel affinity column that was not prepared in the presence of any one of the proteins in the mixture (i.e., a blank column).
Figure 1C:
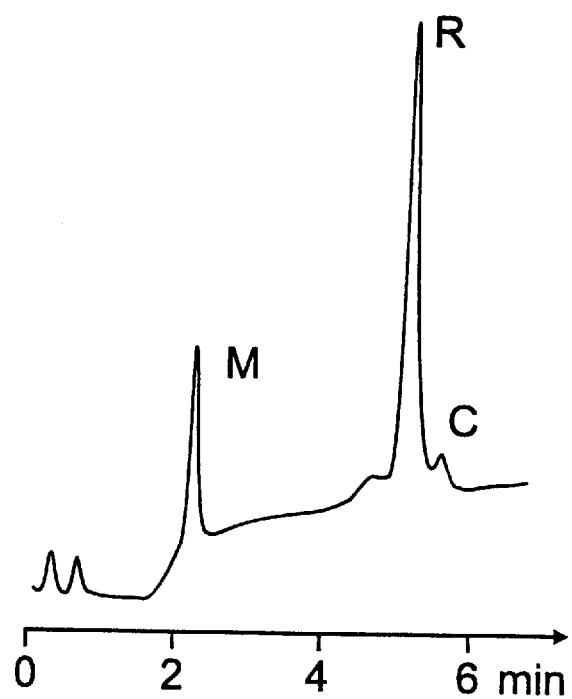
FIG. 1c is a chromatogram of a different non-adsorbed protein fraction of the same test sample, this fraction having been obtained by passing the sample through a gel affinity column that was prepared in the presence of one of the proteins in the mixture (peak "C") in accordance with the present invention.

The chromatogram traces are shown in FIGS. 1a, 1b and 1c. FIG. 1a represents the test mixture; FIG. 1b the non-adsorbed protein fraction from the gel prepared without the use of cytochrome C; and FIG. 1c the non-adsorbed protein fraction from the gel prepared with the use of cytochrome C. The protein peaks are labeled "M" for myoglobin, "R" for ribonuclease, and "C" for cytochrome C. Comparison of FIG. 1a with FIG. 1b shows that these two chromatograms are identical, indicating that the gel prepared without the use of cytochrome C adsorbed none of the three proteins in the test mixture. Comparison of FIG. 1a with FIG. 1c shows that the cytochrome C peak is almost completely missing in FIG. 1c, indicating that the gel prepared with the use of cytochrome C selectively adsorbed cytochrome C.

EXAMPLE 2

This example illustrates the preparation of a polyacrylamide gel with specific affinity for hemoglobin and myoglobin, and the effectiveness of the gel in selectively adsorbing these two proteins relative to cytochrome C and ribonuclease.

The procedure of Example 1 was repeated (producing a polyacrylamide gel with the same values of T and C), except that 10 mg hemoglobin was substituted for the 10 mg cytochrome C in the monomer mixture from which the gel was formed, and the test mixture included hemoglobin (15 mg/mL) in addition to the other three proteins. Both the test mixture (prior to passage through the column) and the non-adsorbed protein fraction (emerging from the column after application and elution of the test mixture) were analyzed on the CB-S HPLC column.

Figure 2A:
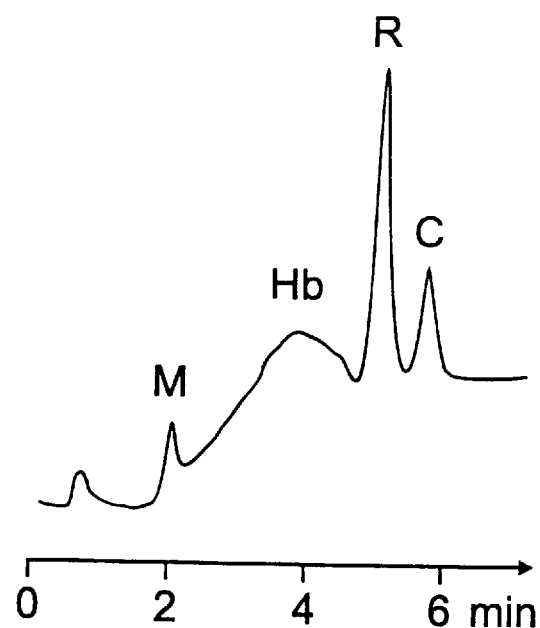
FIG. 2a is a chromatogram of another test sample containing a mixture of proteins prior to passage through a gel affinity column.
Figure 2B:
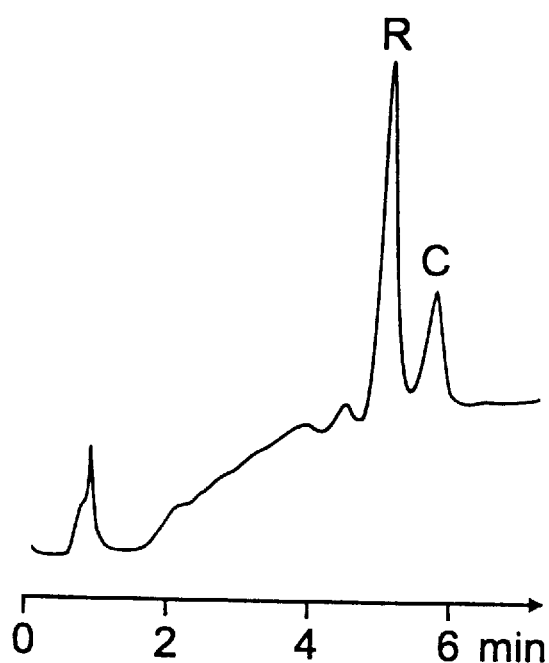
FIG. 2b is a chromatogram of the nonadsorbed protein fraction of the same test sample, obtained by passing the sample through a gel affinity column prepared in the presence of one of the proteins in the mixture (peak "Hb").

The results are shown in the chromatogram traces of FIGS. 2a (test mixture) and 2b (non-adsorbed protein fraction), where the protein peaks are labeled "M" for myoglobin, "Hb" for hemoglobin, "R" for ribonuclease, and "C" for cytochrome C. The absence of both the myoglobin and hemoglobin peaks in the non-adsorbed protein fraction indicates that the gel selectively adsorbed both myoglobin and hemoglobin. The adsorption of myoglobin is due to the fact that hemoglobin consists of four subunits that have a structure similar to that of myoglobin.

EXAMPLE 3

This example reports an experiment to investigate the conditions required for desorption of proteins from a polyacrylamide gel to which the proteins have been specifically adsorbed.

Columns were prepared as described in Examples 1 and 2, one with specific affinity for cytochrome C (per Example 1) and one with specific affinity for hemoglobin (per Example 2). After equilibrating each column with 6 mL of 0.01M sodium phosphate (pH 6.2), cytochrome C (100 $\mu$L of a 5 mg/mL solution) was applied to the cytochrome C-specific column, and hemoglobin and myoglobin (100 $\mu$L each of 5 mg/mL solutions, in separate experiments) were applied to the hemoglobin-specific column. Elutions of the proteins from each column were attempted with 6-mL aliquots of each of the following three solutions:

(a) 0.01M sodium phosphate (pH 6.2) (the equilibration buffer);

(b) 0.01M sodium phosphate (pH 6.2), further containing 0.5M sodium chloride; and (c) 10 volume percent solution of acetic acid containing 10% (weight/volume) sodium dodecyl sulfate.

Eluting fractions of 0.5 mL were collected and analyzed from each test, using the CB-S HPLC column. The results were as follows. Neither cytochrome C, hemoglobin nor myoglobin were eluted from their respective columns with the equilibration buffer alone. Cytochrome C was eluted from the cytochrome C-specific column with solution (b) (the equilibration buffer plus 0.5M sodium chloride), but solution (b) did not result in elution of either hemoglobin or myoglobin from the hemoglobin-specific column. All three proteins—cytochrome C, hemoglobin and myoglobin—were eluted from their respective columns with solution (c).

EXAMPLE 4

This example illustrates the preparation of an agarose gel with specific affinity for hemoglobin, and its effectiveness in selectively adsorbing hemoglobin relative to transferrin.

Low-melting agarose ("EXTRA LM-2" obtained from Hispanagar, Spain, 300 mg) was added to 10 mL of water and dissolved by boiling. The temperature was then lowered to 37° C. and 10 mL of 1M sodium carbonate (pH 11) was added. While the solution was being stirred, sodium borohydride (50 mg), hemoglobin (1 mL of an approximately 30 mg/mL solution in water), and divinyl sulfone (600 $\mu$L) were added. Stirring was continued for 16 hours, and the resulting gel particles were washed with water by centrifugation until the pH of the supernatant had dropped to 6. About 11 g of the gel particles were packed in an HPLC column tube (internal diameter 6 mm; length of gel 1.5 cm), washed with 7 mL of 10% sodium dodecyl sulfate in 10% acetic acid, and finally equilibrated with 0.01M sodium phosphate, pH 7.0. A second column (a control) was also prepared in a manner identical to the first, but without the hemoglobin.

A starting protein solution was prepared for use as a test mixture by combining 2 mg of transferrin dissolved in 500 $\mu$L of 20 mM Tris buffer (tris(hydroxymethyl) aminomethane), pH 8.5, with 250 $\mu$L of a hemoglobin solution (1.5 weight % hemoglobin in water). To each column was applied 3 $\mu$L of the test mixture, and the columns were eluted with 0.05M sodium phosphate (pH 7.0) at a flow rate of 0.05 mL/min. The eluting proteins were collected and analyzed by the CB-S HPLC column used in the preceding examples, with detection at 220 nm.

Figure 3A:
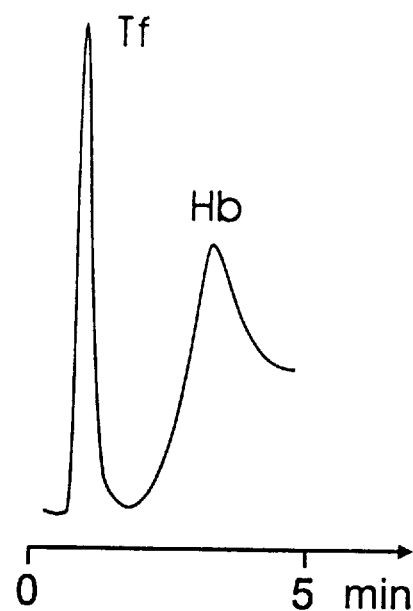
FIG. 3a is a chromatogram of a third test sample containing a different combination of proteins after having been passed through a gel affinity column that was not prepared in the presence of any of the proteins in the sample.
Figure 3B:
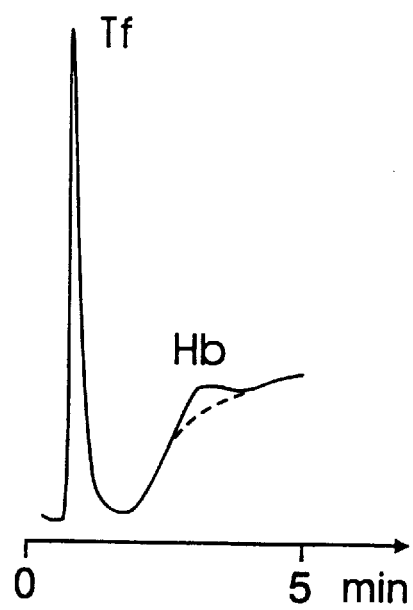
FIG. 3b is a chromatogram of the same test sample after having been passed through a gel affinity column prepared in the presence of one of the proteins in the sample (peak "Hb").

The results are shown in the chromatogram traces of FIGS. 3a and 3b, with the blank column (prepared in the absence of hemoglobin) represented by FIG. 3a and the hemoglobin-specific column represented by FIG. 3b. The peaks are identified in each trace as "Tf" (transferrin) and "Hb" (hemoglobin). Comparison between the two traces shows that the eluate from the hemoglobin-specific column displays a hemoglobin peak that is much smaller relative to the transferrin peak than the hemoglobin peak of the eluate from the blank column. This indicates that the hemoglobin-specific column selectively adsorbs hemoglobin relative to transferrin.

EXAMPLE 5

This example illustrates the preparation of a 2-hydroxyethylmethacrylate/acrylamide gel with specific affinity for hemoglobin, and its effectiveness in selectively adsorbing hemoglobin.

A monomer solution was prepared by dissolving N,N'-methylenebisacrylamide (12.0 mg) and 2-hydroxyethylmethacrylate (4.2 $\mu$L) in 495.8 $\mu$L of 10 mM sodium phosphate (pH 6.2) containing 0.85% (weight/volume) NaCl. Acrylamide (13.5 mg) and ammonium persulfate (5 $\mu$L of a 10% (weight/volume) solution in water) were added, followed by hemoglobin (40 $\mu$L of a 1.5 weight percent solution in water). The resulting mixture was deaerated, then supplemented with 5 $\mu$L of a 5 % (volume/volume) solution of N,N,N',N'-tetramethylethylenediamine and transferred to a 0.6-mL test tube which was maintained at room temperature overnight for polymerization. The resulting gel was broken into small particles by inserting a glass rod into the test tube, then packing the particles into a pasteur pipette as in Example 1. The column was washed with 10 mM sodium phosphate buffer (pH 6.2) containing 0.85% (weight/volume) NaCl, water and 10% sodium dodecyl sulfate (weight/volume) in 10% (volume/volume) acetic acid, and equilibrated with 10 mM sodium phosphate, pH 7.0. This gel was thus formed at a total monomer concentration (T) of 6% and a crosslinker concentration (C) of 40%. The 2-hydroxyethylmethacrylate content, relative to the total of 2-hydroxyethylmethacrylate and acrylamide, was about 25 weight percent.

The column was tested with the same test protein mixture as that used in Example 4, and the results indicated that the column selectively adsorbed hemoglobin relative to transferrin.

EXAMPLE 6

This example shows the use of a proteinase to desorb protein adsorbed onto a gel prepared in accordance with this invention. The protein in this example is ribonuclease adsorbed onto a ribonuclease-specific gel.

Acrylamide (0.0582 g), N,N'-methylenebisacrylamide (0.0018 g) and ribonuclease (0.003 g) were dissolved in 1 mL 0.01M sodium phosphate, pH 7.0. Following addition of 20 $\mu$L of a 10% (weight/volume) solution of ammonium persulfate and deaeration, 20 $\mu$L of a 5% (volume/volume) TEMED solution was added. The polymerization proceeded for thirty minutes, producing a gel with a composition of T=6% and C=3%. Once formed, the gel was pressed through a 60-mesh net to break the gel into granules, and the granules were packed in a pasteur pipette to a height of 4.5 cm. The granules were then washed with 0.8 mL of a solution of Savinase (a proteinase obtained from Novo Nordisk A/S, Denmark), and equilibrated with 3 mL of 10 mM sodium phosphate, pH 7.0. About 50 $\mu$L of a sample solution of hemoglobin (10 mg/mL) and ribonuclease (3 mg/mL) was applied. The column was then washed with 10 mM sodium phosphate, pH 7.0, and a 500-$\mu$L fraction was collected and analyzed by cation-exchange chromatography as described in Example 2.

Figure 4C:
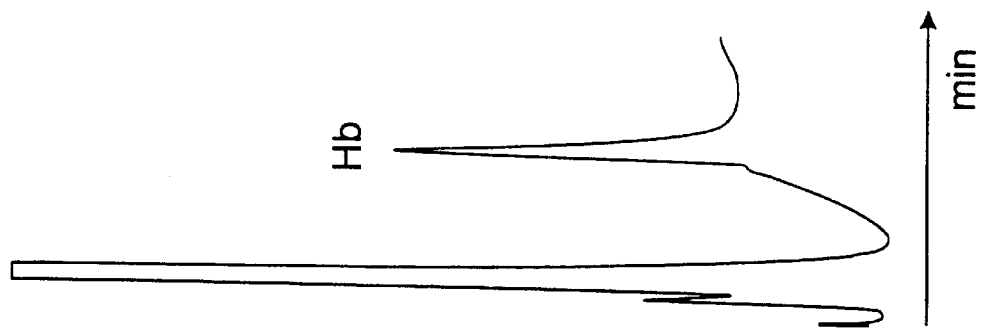
FIG. 4c is a chromatogram of the fraction collected after having passed the sample through a gel affinity column prepared in the presence of one of the proteins in the sample (peak "R").
Figure 4B:
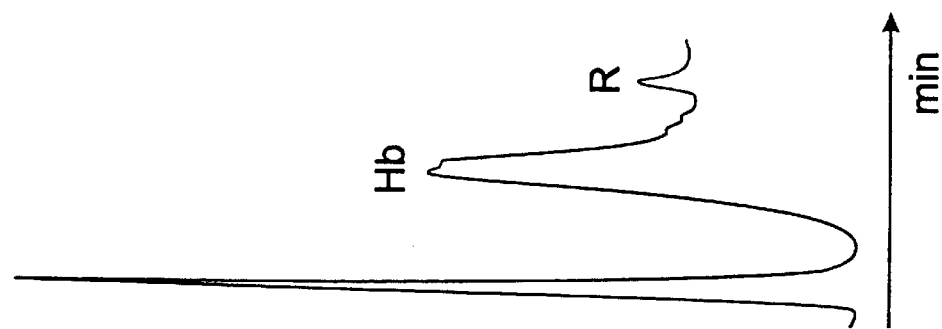
FIG. 4b is a chromatogram of the fraction collected after having passed the sample through a blank column.
Figure 4A:
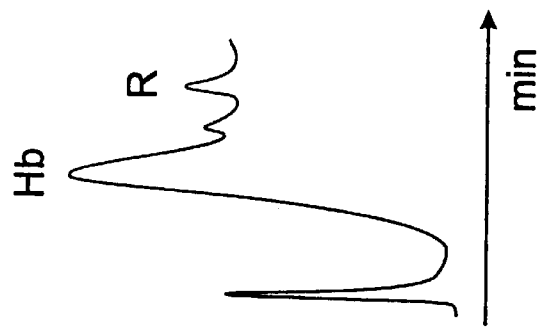
FIG. 4a is a chromatogram of yet another test sample.

The results are shown in the chromatogram traces of FIGS. 4a, 4b and 4c. FIG. 4a is a chromatogram of the sample itself prior to passage through any column ("Hb" designating hemoglobin and "R" designating myoglobin); FIG. 4b is a chromatogram of the fraction collected from a blank column (prepared in the absence of ribonuclease); and FIG. 4c is a chromatogram of the fraction collected from the column prepared in the presence of ribonuclease. The ribonuclease peak is present in FIGS. 4a and 4b but absent in FIG. 4c, indicating that ribonuclease had been specifically adsorbed only by the column prepared in the presence of ribonuclease.

EXAMPLE 7

This example illustrates the high degree of specificity of the adsorption, since only one of two very similar proteins is adsorbed.

Figure 5A:
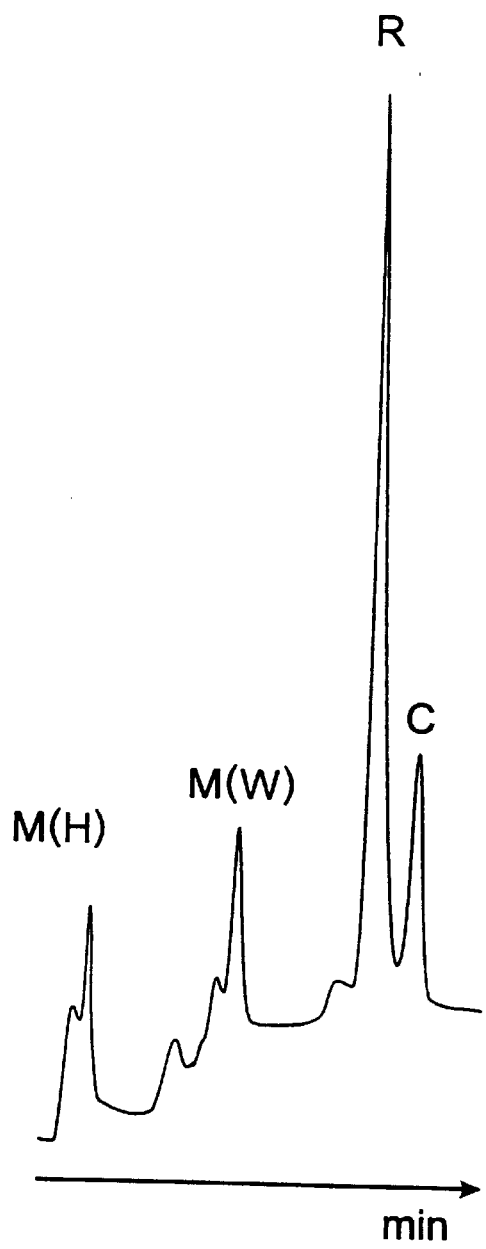
FIG. 5a is a chromatogram of yet another test sample.
Figure 5B:
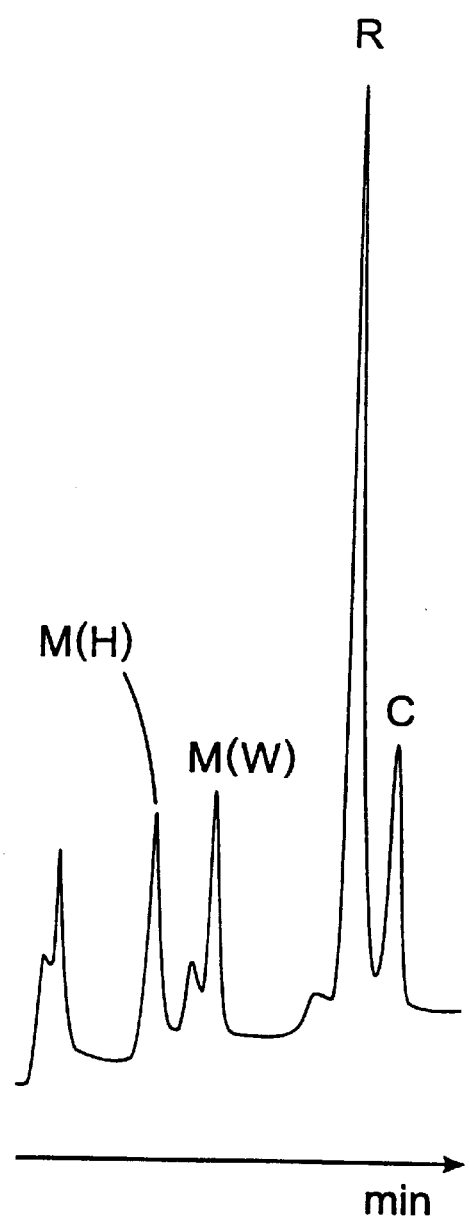
FIG. 5b is a chromatogram of the fraction collected after having been passed through a gel affinity column prepared in the presence of one of the proteins in the sample (peak "M(H)").

A gel specific for horse myoglobin was prepared in a manner analogous to that described in Example 2, with horse myoglobin being substituted for the hemoglobin of Example 2. Separations and analyses were performed as in Example 2, using a test mixture of horse and whale myoglobin, ribonuclease and cytochrome C. The results are shown in FIGS. 5a (fraction collected from the horse myoglobin column) and 5b (fraction collected from a blank column). In these chromatograms, "M(H)" designates horse myoglobin, "M(W)" designates whale myoglobin, "R" designates ribonuclease, and "C" designates cytochrome C.

A comparison between the two chromatograms shows that the horse myoglobin column had specificity for horse myoglobin, and did not adsorb whale myoglobin. This indicates a very high degree of specificity since the amino acid composition of the two myoglobins differs in only twenty of the 153 amino acids and in such a way that the 3-dimensional structure is only slightly affected.

EXAMPLE 8

This example demonstrates that the use of functional monomers in accordance with the teachings of Mosbach et al. decreases the selectivity of the gel. As explained above, this is due to the random distribution of the functional monomer residue throughout the polymer chains in the gel, and the fact that very few if any of the functional monomers occupy a position corresponding to a complementary group in the solute. The column therefore acts as an ion exchanger if the residue is charged, as in the experiment presented in this example. Salt can be added to suppress the electrostatic interactions, but specific interactions are lost and non-specific hydrophobic interactions will occur to an increasing degree as the salt concentration increases.

Acrylamide (0.114 g), N,N'-methylenebisacrylamide (0.012 g), and acrylic acid (0.114 mL) were dissolved in 4 mL 0.01M sodium phosphate, pH 7.0. The pH was adjusted with 2M NaOH to 7.0 (the presence of acrylic acid lowers the pH). Following addition of 4.0 µL of a 10% (weight/volume) solution of ammonium persulfate, 0.1 mL of a 1.5% solution of hemoglobin was added. After deaeration, 40 µL of a 5% (volume/volume) solution of TEMED was added to initiate the polymerization, which was permitted to proceed overnight. As in previous examples, blank control columns were prepared in the same way but without hemoglobin present.

The gel, which had a composition of T=6% and C=5%, was pressed through a 30-mesh net to form granules that were then packed into pasteur pipettes to form columns having heights of 5.5 cm. One column was washed with 10% SDS in 10% acetic acid to desorb hemoglobin. It was very difficult to remove SDS from the column, however, which is one disadvantage of this acrylic acid-containing bed. A second column was therefore washed instead with 0.02M sodium phosphate buffer, pH 7.0, containing 80% (volume/volume) ethylene glycol and 0.5M sodium chloride. This column was then washed with 0.01M sodium phosphate, pH 6.2, plus 0.5M NaCl, and 10 µL of a protein sample (2 mg/mL of transferrin and 15 mg/mL of hemoglobin) was applied. The column was eluted with the 0.01M sodium phosphate, pH 6.2 buffer, containing 0.5M HCl, and the eluate was analyzed as in previous examples.

Figure 6A:
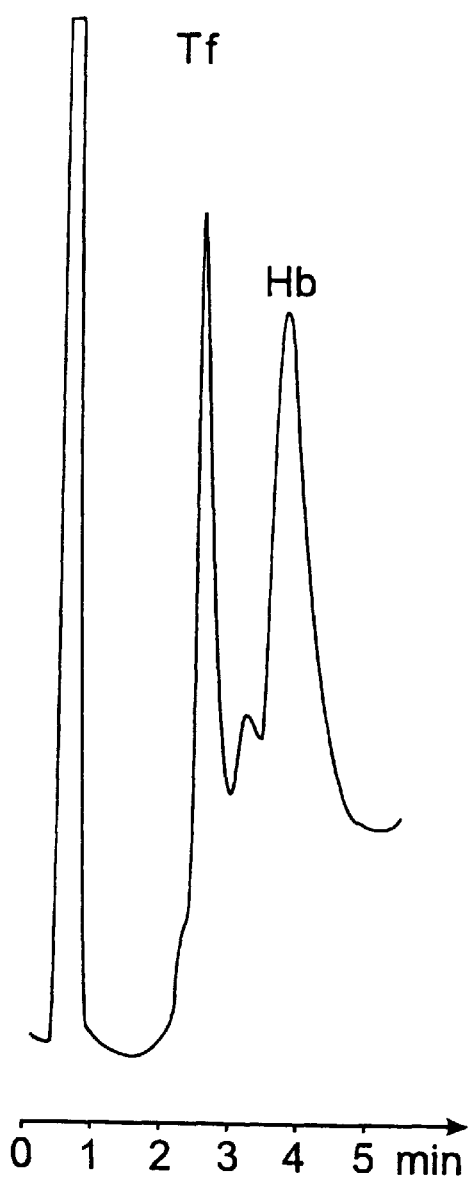
FIGS. 6a, 6b and 6c represent the prior art teachings of Mosbach et al.
Figure 6B:
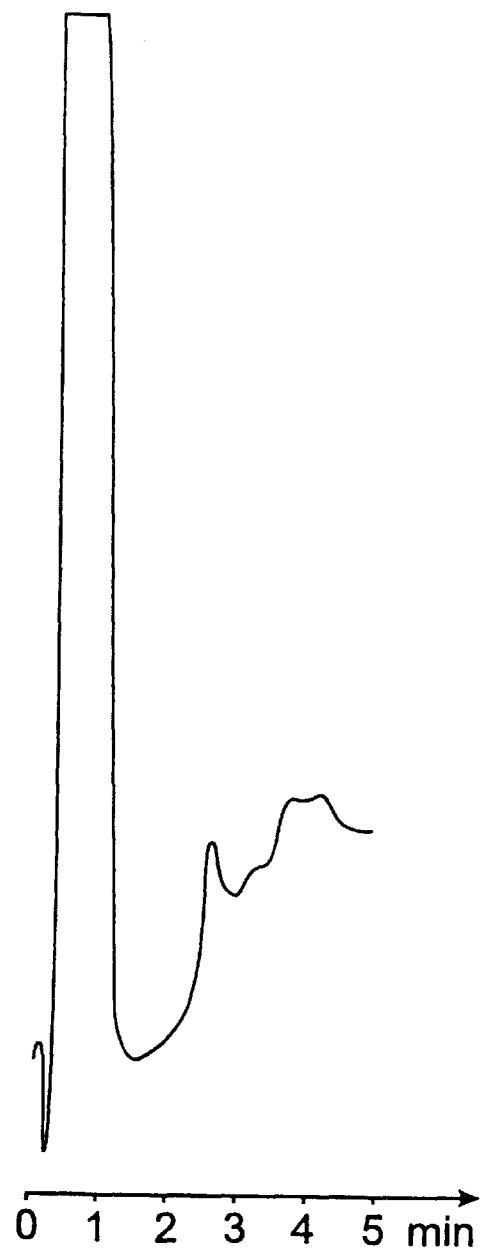
Figure 6C:
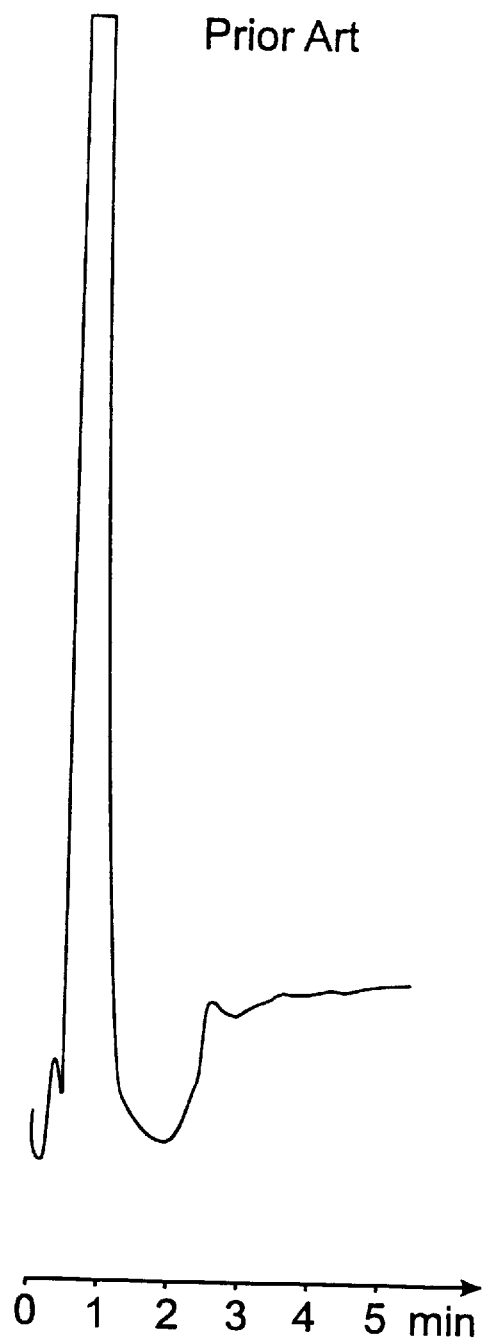

Chromatograms are presented in FIGS. 6a (the sample prior to application to either column, where "Tf" designates transferrin and "Hb" designates hemoglobin), 6b (fraction collected from a blank column, using 0.01M sodium phosphate, pH 6.2, containing 0.5M NaCl for the elution) and 6c (fraction collected from the second column). A comparison of the three figures shows that the imprinted column adsorbed both hemoglobin and transferrin. The specificity of the column for hemoglobin was thus completely lost when the functional monomer acrylic acid was incorporated into the gel bed.

The foregoing is offered primarily for purposes of illustration. It will be readily apparent to those skilled in the art that the materials, proportions, operating conditions, procedural steps and other parameters of this invention may be further modified or substituted in various ways without departing from the spirit and scope of the invention.

We claim:

1. A method for preparing an affinity chromatography medium with selective affinity for a preselected species, said method comprising:
   (a) forming a insoluble polymer matrix from a polymerizable substance in the presence of said preselected species, said polymerizable substance being non-ionizable and one with respect to which said preselected species is inert; and
   (b) extracting said preselected species from said insoluble polymer matrix.

2. A method in accordance with claim 1 in which said polymerizable substance is a member selected from the group consisting of acrylamide, agarose, methacrylate, substituted acrylamides and substituted methacrylates.

3. A method in accordance with claim 1 in which said polymerizable substance is a member selected from the group consisting of acrylamide, agarose, methacrylate, methyl methacrylate, and 2-hydroxyethyl methacrylate.

4. A method in accordance with claim 1 in which (a) is performed in aqueous solution at a polymerizable substance concentration of about 1% to about 60% by weight.

5. A method in accordance with claim 1 in which (a) is performed in the presence of a crosslinking agent.

6. A method in accordance with claim 1 in which said crosslinking agent is present in an amount ranging from about 0.2% to about 60% by weight relative to said polymerizable substance and said crosslinking agent combined.

7. A method in accordance with claim 1 in which said polymerizable substance is acrylamide and (a) is conducted in the further presence of a member selected from the group consisting of N,N'-methylenebisacrylamide, piperazinediacrylamide, N,N'-bisacrylylcystamine, and N,N'-diallyltartardiamide.

8. A method in accordance with claim 1 in which said polymerizable substance is agarose and (a) is conducted in the further presence of a member selected from the group consisting of divinyl sulfone and bis-epoxides.

9. A method in accordance with claim 1 in which said polymerizable substance is a mixture of 2-hydroxyethylmethacrylate and acrylamide and (a) is conducted in the further presence of N,N'-methylenebisacrylamide.

10. A method in accordance with claim 1 in which said preselected species is a molecule having a molecular weight of from about 100 to about 1,000,000.

11. A method in accordance with claim 1 in which said preselected species is a member selected from the group consisting of proteins, viruses, bacteria, nucleic acids, and carbohydrates.

12. A method in accordance with claim 1 in which (b) is performed by treating said insoluble polymer matrix with a member selected from the group consisting of salts, detergents, ethylene glycol and enzymes.

* * * * *